United States Patent [19]

Sick et al.

[11] Patent Number: 5,281,530
[45] Date of Patent: Jan. 25, 1994

[54] **GENES ENCODING NEMATODE-ACTIVE TOXINS CLONED FROM *BACILLUS THURINGIENSIS* ISOLATE PS17**

[75] Inventors: August J. Sick, Oceanside; George E. Schwab, La Jolla; Jewel M. Payne, San Diego, all of Calif.

[73] Assignee: Mycogen Corporation, San Diego, Calif.

[21] Appl. No.: 557,246

[22] Filed: Jul. 24, 1990

Related U.S. Application Data

[63] Continuation-in-part of Ser. No. 535,810, Jun. 11, 1990, abandoned, which is a continuation-in-part of Ser. No. 84,653, Aug. 12, 1987, Pat. No. 4,948,734.

[51] Int. Cl.$^5$ .................... C12N 1/20; C12N 15/00; A01N 63/00
[52] U.S. Cl. ...................... 435/252.3; 435/320.1; 435/252.33; 435/240.4; 536/23.71; 530/350; 935/9; 424/93 L
[58] Field of Search ............ 536/27; 435/320.1, 252.3, 435/252.33; 530/350; 935/9; 424/93

[56] References Cited

PUBLICATIONS

Prichard, R. K., C. A. Hall, J. D. Kelly, I. C. A. Martin, and A. D. Donald (1980) "The Problem of Anthelmintic Resistance in Nematodes," Austr. Vet. J. 56:239–251.

Coles, G. C. (1986) "Anthelmintic Resistance in Sheep," In *Veterinary Clinics of North America: Food Animal Practice*, vol. 2:423–432 (Herd, R. P., ed.), W. B. Saunders, New York.

Bottjer, K. P., L. W. Bone, and S. S. Gill (1985) "Nematoda: Susceptibility of the Egg to *Bacillus thuringiensis* Toxins," Experimental Parisitology 60:239–244.

Ignoffo, C. M., and V. H. Dropkin (1977) "Deleterious Effects of the Thermostable Toxin of *Bacillus thuringiensis* on Species of Soil–Inhabiting, Myceliophagus, and Plant-Parasitic Nematodes," J. Kansas Entomol. Soc. 50:394–398.

Ciordia, H., and W. E. Bizzell (1961) "A Preliminary Report on the Effects of *Bacillus thuringiensis* var. *thuringiensis* Berliner on the Development of the Free-Living Stages of Some Cattle Nematodes;" J. Parisitol. 47:41 (abstract).

Prefontaine et al., *App. Env. Mic.*, vol. 53, #12, pp. 2808–2814, Dec. 1987.

Haider, et al. Gene, 52, pp. 285–290, 1987.

*Primary Examiner*—Robert A. Wax
*Assistant Examiner*—Keith D. Hendricks
*Attorney, Agent, or Firm*—Saliwanchik & Saliwanchik

[57] ABSTRACT

Nematicidal δ-endotoxin encoding genes have been cloned from a novel *Bacillus thuringiensis* isolate known as B.t. PS17. These novel genes, designated B.t. PS17a, B.t. PS17b, Bt. PS17d, and B.t. PS17e, can be transferred to various microbial and plant hosts via known techniques. In the microbial or plant host, one or more of the genes of the invention can be used to express the novel nematicidal toxins to control susceptible nematodes.

15 Claims, 26 Drawing Sheets

```
Met Ala Ile Leu Asn Glu Leu Tyr Pro Ser Val Pro Tyr Asn Val Leu
 1                   5                  10                  15
Ala Tyr Thr Pro Leu Phe Ser Phe Leu Pro Asp Leu Tyr Pro Thr Gln Ala Thr
        20                  25                      30
Pro Ala Asp Leu Thr Ala Tyr Glu Gln Leu Lys Asn Lys Leu Glu Lys
            35                  40                  45
Gly Ile Asn Ala Gly Thr Tyr Ser Lys Ala Ile Ala Asp Val Leu Lys
        50                  55                  60
Gly Ile Phe Ile Asp Asp Thr Ile Asn Tyr Gln Thr Tyr Val Asn Ile
65          70                  75                      80
Gly Leu Ser Leu Ile Thr Leu Ala Val Pro Glu Ile Gly Ile Phe Thr
                85                  90                  95
Pro Phe Ile Gly Leu Phe Ala Ala Leu Asn Lys His Ala Pro Ala Pro
                100                 105                 110
Pro Pro Asn Ala Lys Asp Ile Phe Glu Ala Met Lys Pro Pro Ala Ile
            115                 120                 125
Gln Glu Met Ile Asp Arg Thr Leu Thr Ala Asp Glu Gln Thr Phe Leu
        130                 135                 140
Asn Gly Glu Ile Ser Gly Leu Gln Asn Leu Ala Ala Arg Tyr Gln Ser
145                 150                 155                 160
Thr Met Asp Ile Gln Ser His Gly Gly Phe Asn Lys Val Asp Ser
            165                 170                 175
Gly Leu Ile Lys Lys Phe Thr Asp Glu Val Leu Ser Leu Asn Ser Phe
        180                     185                 190
Tyr Thr Arg Ala Leu Pro Val Phe Ile Thr Asp Asn Thr Ala Asp Arg
            195                 200                 205
Thr Leu Leu Gly Leu Pro Tyr Tyr Ala Ile Leu Ala Ser Met His Leu
        210                 215                 220
Met Leu Leu Arg Asp Ile Thr Lys Gly Pro Thr Trp Asp Ser Lys
225                 230                 235                 240
Ile Asn Phe Thr Pro Asp Ala Ile Asp Ser Phe Lys Thr Asp Ile Lys
            245                 250                 255
Asn Asn Ile Lys Leu Tyr Ser Lys Thr Ile Tyr Asp Val Phe Gln Lys
        260                 265                 270
Gly Leu Ala Ser Tyr Gly Thr Pro Pro Ser Asp Leu Glu Ser Phe Ala Lys
275                 280                 285
Lys Gln Lys Tyr Ile Glu Met Ile Thr Thr His Cys Leu Asp Phe Ala
        290                 295                 300
```

Figure 1A

```
Arg Leu Phe Pro Thr Phe Asp Pro Leu Tyr Pro Thr Gly Ser Gly
305                 310                 315                 320
Asp Ile Ser Leu Gln Lys Thr Arg Arg Ile Leu Ser Pro Ile Pro
                325                 330                 335
Ile Arg Thr Ala Asp Gly Leu Thr Leu Asn Asn Thr Ser Ile Asp Thr
        340                 345                 350
Ser Asn Trp Pro Asn Tyr Glu Asn Gly Ala Phe Pro Asn Pro
        355                 360         365
Lys Glu Arg Ile Leu Lys Gln Phe Lys Leu Tyr Ser Trp Arg Ala
    370                 375                 380
Gly Gln Tyr Gly Gly Leu Leu Gln Pro Tyr Leu Trp Ala Ile Glu Val
385                 390                 395                 400
Gln Asp Ser Val Glu Thr Arg Leu Tyr Gln Leu Pro Ala Val Asp
        405                 410             415
Pro Gln Ala Gly Pro Asn Tyr Val Ser Ile Thr Pro Asn Pro Ile
                420                 425                 430
Ile Gln Ile Asn Met Asp Thr Lys Thr Pro Gln Gly Ala Ser
        435                 440         445
Gly Trp Asn Thr Asn Leu Met Arg Gly Ser Val Ser Gly Leu Ser Phe
450                 455                 460
Leu Gln Arg Asp Gly Thr Arg Ala Leu Ser Ala Gly Met Gly Gly Phe
465                 470                 475             480
Ala Asp Thr Ile Tyr Ser Tyr His Thr Tyr Leu Ser Tyr Leu
                485                 490         495
Tyr Gly Thr Pro Tyr Gln Thr Ser Asp Asn Tyr Ser Gly His Val Gly
500                 505                 510
Ala Leu Val Gly Val Ser Thr Pro Gln Glu Ala Thr Leu Pro Asn Ile
515                 520             525
Ile Gly Gln Pro Asp Gly Gln Gly Asn Val Ser Thr Met Gly Phe Pro
530                 535                 540
Phe Glu Lys Ala Ser Gly Gly Thr Val Lys Glu Trp Leu Asn
545                 550             555             560
Gly Ala Asn Ala Met Lys Leu Ser Pro Gln Ser Ile Gly Ile Pro
        565                 570         575
Ile Thr Asn Val Thr Ser Gly Glu Tyr Tyr Gln Ile Arg Arg Cys Tyr Ala
        580                 585                 590
Ser Asn Asp Asn Thr Asn Val Phe Phe Asn Val Asp Thr Gly Ala
595                 600                 605
```

Figure 1B

Asn Pro Ile Phe Gln Gln Ile Asn Phe Ala Ser Thr Val Asp Asn Asn
    610             615             620
Thr Gly Val Gln Gly Ala Asn Gly Val Tyr Val Lys Ser Ile Ala
625             630             635             640
Thr Thr Asp Asn Ser Phe Thr Glu Ile Pro Ala Lys Thr Ile Val
                645             650             655
His Leu Thr Asn Gln Gly Ser Ser Phe Leu Asp Arg Ile Glu
660             665             670
Phe Ile Pro Phe Ser Leu Pro Leu Ile Tyr His Gly Ser Tyr Asn Thr
    675             680             685
Ser Ser Gly Ala Asp Asp Val Leu Trp Ser Ser Asn Met Asn Tyr
690             695             700
Tyr Asp Ile Ile Val Asn Gly Gln Ala Asn Ser Ser Ile Ala Ser
705             710             715             720
Ser Met Met His Leu Leu Lys Gly Lys Val Ile Thr Ile Lys Ser
                725             730             735
Pro Gly His Ser Glu Thr Phe Phe Ala Thr Pro Phe Pro Val Pro Glu Gly Gly
740             745             750
Phe Asn Glu Val Arg Ile Leu Gly Leu Ala Gly Leu Pro Glu Val Ser Gly Asn
755             760             765
Ile Thr Val Gln Ser Asn Asn Pro Pro Gln Pro Ser Asn Asn Gly Gly
770             775             780
Gly Asp Gly Gly Gly Asn Gly Gly Asp Gly Gly Gly Tyr Gln Tyr Asn Phe
785             790             795             800
Ser Leu Ser Gly Ser Asp His Thr Thr Ile Tyr His Gly Lys Leu Glu
805             810             815
Thr Gly Ile His Val Gln Gly Asn Tyr Tyr Tyr Thr Val Val Ser Ser Pro Val
                820             825             830
Leu Ile Leu Asn Ala Tyr Arg Asn Asn Thr Val Val Ser Ser Ile Pro
835             840             845
Val Tyr Ser Pro Phe Asp Ile Thr Ile Gln Thr Glu Ala Asp Ser Leu
850             855             860
Glu Leu Glu Leu Gln Pro Arg Tyr Gly Phe Ala Thr Val Asn Gly Thr
865             870             875             880
Ala Thr Val Lys Ser Pro Asn Val Asn Tyr Asp Arg Ser Phe Lys Leu
                885             890             895
Pro Ile Asp Leu Gln Asn Ile Thr Thr Gln Val Asn Ala Leu Phe Ala
900             905             910

Figure 1C

```
Ser Gly Thr Gln Asn Met Leu Ala His Asn Val Ser Asp His Asp Ile
        915             920             925
Glu Glu Val Val Leu Lys Val Asp Ala Leu Ser Asp Glu Val Phe Gly
930             935             940
Asp Glu Lys Lys Ala Leu Arg Lys Leu Val Asn Gln Ala Lys Arg Leu
945             950             955             960
Ser Arg Ala Ala Arg Asn Leu Leu Ile Gly Ser Phe Glu Asn Trp Asp
                965             970             975
Ala Trp Tyr Lys Gly Arg Asn Val Val Thr Val Ser Asp His Glu Leu
        980             985             990
Phe Lys Ser Asp His Val Leu Leu Pro Pro Pro Gly Leu Ser Pro Ser
        995             1000            1005
Tyr Ile Phe Gln Lys Val Glu Gly Ser Lys Leu Lys Pro Asn Thr Arg
        1010            1015            1020
Tyr Ile Val Ser Gly Phe Ile Ala His Gly Lys Asp Leu Glu Ile Val
1025            1030            1035            1040
Val Ser Arg Tyr Gly Gln Glu Gly Val Lys Val Val Gln Val Pro Tyr
                1045            1050            1055
Gly Glu Ala Phe Pro Leu Thr Ser Asn Gly Pro Val Cys Cys Pro Pro
        1060            1065            1070
Arg Ser Thr Ser Asn Gly Thr Leu Gly Asp Pro His Phe Phe Ser Tyr
        1075            1080            1085
Ser Ile Asp Val Gly Ala Leu Asp Leu Gln Ala Asn Pro Gly Ile Glu
        1090            1095            1100
Phe Gly Leu Arg Ile Val Asn Pro Thr Gly Met Ala Arg Val Ser Asn
1105            1110            1115            1120
Leu Glu Ile Arg Glu Asp Arg Pro Leu Ala Ala Asn Glu Ile Arg Gln
                1125            1130            1135
Val Gln Arg Val Ala Arg Asn Trp Arg Thr Glu Tyr Glu Lys Glu Arg
        1140            1145            1150
Ala Glu Val Thr Ser Leu Ile Gln Pro Val Ile Asn Arg Ile Asn Gly
        1155            1160            1165
Leu Tyr Glu Asn Gly Asn Trp Asn Gly Ser Ile Arg Ser Asp Ile Ser
1170            1175            1180
```

Figure 1D

```
Tyr Gln Asn Ile Asp Ala Ile Val Leu Pro Thr Leu Pro Lys Leu Arg
1185                1190                1195                1200
His Trp Phe Met Ser Asp Arg Phe Ser Glu Gln Gly Asp Ile Met Ala
                1205                1210                1215
Lys Phe Gln Gly Ala Leu Asn Arg Ala Tyr Ala Gln Leu Glu Gln Ser
        1220                1225                1230
Thr Leu Leu His Asn Gly His Phe Lys Thr Lys Asp Ala Ala Asn Trp Thr
            1235                1240                1245
Ile Glu Gly Asp Ala His Gln Ile Thr Leu Glu Asp Gly Arg Arg Val
    1250                1255                1260
Leu Arg Leu Pro Asp Trp Ser Ser Ser Val Ser Gln Met Ile Glu Ile
1265                1270                1275                1280
Glu Asn Phe Asn Pro Asp Lys Glu Tyr Asn Leu Val Phe His Gly Gln
            1285                1290                1295
Gly Glu Gly Thr Val Thr Leu Glu His His Gly Glu Thr Lys Tyr Ile
        1300                1305                1310
Glu Thr His His His Phe Ala Asn Phe Thr Thr Ser Gln Arg Gln
            1315                1320                1325
Gly Leu Thr Phe Glu Leu Ser Asn Lys Val Thr Val Thr Ile Ser Ser Glu
    1330                1335                1340
Asp Gly Glu Phe Leu Val Asp Asn Ile Ala Leu Val Glu Ala Pro Leu
1345                1350                1355                1360
Pro Thr Asp Asp Gln Asn Ser Glu Gly Asn Thr Ala Ser Ser Thr Asn
            1365                1370                1375
Ser Asp Thr Ser Met Asn Asn Asn Gln
            1380                1385
```

Figure 1E

| | | | | |
|---|---|---|---|---|
| ATGGCAATTT | TAAATGAATT | ATATCCATCT | GTACCTTATA | ATGTATTGGC | GTATACGCCA | 60 |
| CCCTCTTTT | TACCTGATGC | GGGTACACAA | GCTACACCTG | CTGACTTAAC | AGCTTATGAA | 120 |
| CAATTGTTGA | AAAATTAGA | AAAAGGGATA | AATGCTGAAA | CTTATTCGAA | AGCAATAGCT | 180 |
| GATGTACTTA | AAGTATTTT | TATAGATGAT | ACAATAAAATT | ATCAAACATA | TGTAAATATT | 240 |
| GGTTTAAGTT | TAATTACATT | AGCTGTACCG | GAAATTGGTA | TTTTACACC | TTTCATCGGT | 300 |
| TTGTTTTTG | CTGCATTGAA | TAAACATGAT | GCTCCACCTC | CTCCTAATGC | AAAAGATATA | 360 |
| TTTGAGGCTA | TGAAACCAGC | GATTCAAGAG | ATGATTGATA | GAACTTTAAC | TGCCGGATGAG | 420 |
| CAAACATTTT | TAAATGGGGA | AATAAGTGGT | TTACAAAATT | TAGCAGCAAG | ATACCAGTCT | 480 |
| ACAATGGATG | ATATTCAAAG | CCATGGAGGA | TTTAATAAGG | TAGATTCTGG | ATTAATTAAA | 540 |
| AAGTTTACAG | ATGAGGTACT | ATCTTTAAAT | AGTTTTTATA | CAGATCGTTT | ACCTGTATTT | 600 |
| ATTACAGATA | ATACAGCGGA | TCGAACTTTG | TTAGGTCTTC | TATTATTG | TATACTTGCG | 660 |
| AGCATGCATC | TTATGTTATT | AAGAGATATC | ATTACTAAGG | GTCCGACATG | GGATTCTAAA | 720 |
| ATTAATTTCA | CACCAGATGC | AATTGATTCC | TTTAAAACCG | ATATTAAAAA | TAATATAAAG | 780 |
| CTTTACTCTA | AAACTATTTA | TGACGTATTT | CAGAAGGGAC | TTGCTTCATA | CGGAACGCCT | 840 |

Figure 2A

```
TCTGATTTAG AGTCCTTTGC AAAAAAACAA AAATATATTG AAATTATGAC AACACATTGT    900
TTAGATTTTG CAAGATTGTT TCCTACTTTT GATCCAGATC TTTATCCAAC AGGATCAGGT    960
GATATAAGTT TACAAAAAAC ACGTAGAATT CTTTCTCCTT TTATCCCTAT ACGTACTGCA   1020
GATGGGTTAA CATTAAATAA TACTTCAATT GATACTTCAA ATTGGCCTAA TTATGAAAAT   1080
GGGAATGGCG CGTTTCCAAA CCCAAAAGAA AGAATATTAA AACAATTCAA ACTGTATCCT   1140
AGTTGGAGAG CGGGACAGTA CGGTGGGCTT TTACAACCTT ATTTATGGGC AATAGAAGTC   1200
CAAGATTCTG TAGAGACTCG TTTGTATGGG CAGCTTCCAG CTGTAGATCC ACAGGCAGGG   1260
CCTAATTATG TTTCCATAGA TTCTTCTAAT CCAATCATAC AAATAAATAT GGATACTTGG   1320
AAAACACCAC CACAAGGTGC GAGTGGGTGG AATACAAATT TAATGAGAGG AAGTGTAAGC   1380
GGGTTAAGTT TTTTACAACG AGATGGTACG CCCTGCAACT CATTATCTTT CTGGTATGGG   1440
GCTGATACAA TATATAGTCT CTGATAACTA CATTATCTTT CTTATCTCTA TGGAACTCCT   1500
TATCAAACTT CTGATAACTA TTCTGGTCAC GTTGGTGCAT TGGTAGGTGT GAGTACGCCT   1560
CAAGAGGCTA CTCTTCCTAA TATTATAGGT CAACCAGATG AACAGGGAAA TGTATCTACA   1620
```

Figure 2B

| | | | | |
|---|---|---|---|---|
| ATGGGATTTC | CGTTTGAAAA | AGCTTCCTAT | GGAGGTACAG | TTGTTAAAGA | ATGGTTAAAT | 1680 |
| GGTGCGAATG | CGATGAAGCT | TTCTCCTGGG | CAATCTATAG | GTATTCCTAT | TACAAATGTA | 1740 |
| ACAAGTGGAG | AATATCAAAT | TCGTGTGTCGT | TATGCAAGTA | ATGATAAATAC | TAACGTTTTC | 1800 |
| TTTAATGTAG | ATACTGGTGG | AGCAAATCCA | ATTTTCCAAC | AGATAAACTT | TGCATCTACT | 1860 |
| GTAGATAATA | ATACGGGAGT | ACAAGGAGCA | AATGGTGTCT | ATGTAGTCAA | ATCTATTGCT | 1920 |
| ACAACTGATA | ATTCTTTTAC | AGAAATTCCT | GCGAAGACGA | TTAATGTTCA | TTTAACCAAC | 1980 |
| CAAGGTTCTT | CTGATGTCTT | TTTAGACCGT | ATTGAATTTA | TACCTTTTTC | TCTACCTCTT | 2040 |
| ATATATCATG | GAAGTTATAA | TACTTCATCA | GGTGCAGATG | ATGTTTTATG | GTCTTCTTCA | 2100 |
| AATATGAATT | ACTACGATAT | AATAGTAAAT | GGTCAGGCCA | ATAGTAGTAG | TATCGCTAGT | 2160 |
| TCTATGCATT | TGCTTAATAA | AGGAAAAGTG | ATAAAAACAA | TTGATATTCC | AGGGCATTCG | 2220 |
| GAAACCTTCT | TTGCTACGTT | CCCAGTTCCA | GAAGGATTTA | ATGAAGTTAG | AATTCTTGCT | 2280 |
| GGCCTTCCAG | AAGTTAGTGG | AAATATTACC | GTACAATCTA | ATAATCCGCC | TCAACCTAGT | 2340 |

Figure 2C

```
AATAATGGTG GTGGTGATGG TGGTGGTAAT GGTGGTGGTG ATGGTGGTCA ATACAATTTT   2400
TCTTTAAGCG GATCTGATCA TACGACTATT TATCATGGAA AACTTGAAAC TGGGATTCAT   2460
GTACAAGGTA ATTATACCTA TACAGGTACT CCCGTATTAA TACTGAATGC TTACAGAAAT   2520
AATACTGTAG TATCAAGCAT TCCAGTATAT TCTCCTTTTG ATATAACTAT ACAGACAGAA   2580
GCTGATAGCC TTGAGCTTGA ACTACAACCT AGATATGGTT TTGCCACAGT GAATGGTACT   2640
GCAACAGTAA AAAGTCCTAA TGTAAATTAC GATAGATCAT TTAAACTCCC AATAGACTTA   2700
CAAAATATCA CAACACAAGT AAATGCATTA TTCGCATCTG GAACACAAAA TATGCTTGCT   2760
CATAATGTAA GTGATCATGA TATTGAAGAA GTTGTATTAA AAGTGGATGC CTTATCAGAT   2820
GAAGTATTTG GAGATGAGAA GAAGGCTTTA CGTAAAATTGG TGAATCAAGC AAAACGTTTG   2880
AGTAGAGCAA GAAATCTTCT GATAGGTGGG AGTTTTGAAA ATTGGGATGC ATGGTATAAA   2940
GGAAGAAATG TAGTAACTGT ATCTGATCAT GAACTATTTA AGAGTGATCA TGTATTATTA   3000
```

Figure 2D

```
CCACCACCAG GATTGTCTCC ATCTTATATT TTCCAAAAAG TGGAGGAATC TAAATTAAAA   3060
CCAAATACAC GTTATATTGT TTCTGGATTC ATCGCACATG GAAAAGACCT AGAAATTGTT   3120
GTTTCACGTT ATGGGCAAGA AGTGCAAAAG GTCGTGCAAG TTCCTTATGG AGAAGCATTC   3180
CCGTTAACAT CAAATGGACC AGTTTGTTGT CCCCCACGTT CTACAAGTAA TGGAACCTTA   3240
GGAGATCCAC ATTTCTTTAG TTACAGTATC GATGTAGGTG CACTAGATTT ACAAGCAAAC   3300
CCTGGTATTG AATTTGGTCT TCGTATTGTA AATCCAACTG GAATGGCACG CGTAAGCAAT   3360
TTGGAAATTC GTGAAGATCG TCCATTAGCA TACGACAAGT ACAACGTGTC   3420
GCAAGAAATT GGAGAACCGA GTATGAGAAA GAACGTGCGG AAGTAACAAG TTTAATTCAA   3480
CCTGTTATCA ATCGAATCAA CGGATTGTAT GAAAATGGAA ATTGGAACGG TTCTATTCGT   3540
TCAGATATTT CGTATCAGAA TATAGACGCG ATTGTATTAC CAACGTTACC AAAGTTACGC   3600
CATTGGTTTA TGTCAGATAG ATTCAGTGAA CAAGGAGATA TAATGGCTAA ATTCCAAGGT   3660
```

Figure 2E

```
GCATTAAATC GTGCGTATGC ACAACTGGAA CAAAGTACGC TTCTGCATAA TGGTCATTTT  3720
ACAAAGATG  CAGCTAATTG GACAATAGAA GGCGATGCAC ATCAGATAAC ACTAGAAGAT  3780
GGTAGACGTG TATTGCGACT TCCAGATTGG TCTTCGAGTG TATCTCAAAT GATTGAAATC  3840
GAGAATTTTA ATCCAGATAA AGAATACAAC TTAGTATTCC ATGGGCAAGG AGAAGGAACG  3900
GTTACGTTGG AGCATGGAGA AGAAACAAAA TATATAGAAA CGCATACACA TCATTTTGCG  3960
AATTTACAA  CTTCTCAACG TCAAGGACTC ACGTTTGAAT CAAATAAAGT GACAGTGACC  4020
ATTTCTTCAG AAGATGGAGA ATTCTTAGTG GATAATATTG CGCTTGTGGA AGCTCCTCTT  4080
CCTACAGATG ACCAAAATTC TGAGGGAAAT ACGGCTTCCA GTACGAATAG CGATACAAGT  4140
ATGAACAACA ATCAA                                                  4155
```

Figure 2F

```
                             5                    10                   15
  1 Met Ala Ile Leu Asn Glu Leu Tyr Pro Ser Val Pro Tyr Asn Val
 16 Leu Ala Tyr Thr Pro Ser Phe Leu Tyr Pro Asp Ala Gly Thr Gln
 31 Ala Thr Pro Ala Asp Leu Asn Thr Tyr Glu Gln Leu Leu Lys Asn
 46 Leu Glu Lys Gly Ile Ala Asn Ala Gly Thr Tyr Ser Lys Ala Ile
 61 Asp Val Leu Lys Gly Ile Phe Gly Ile Asp Ile Leu Asn Tyr Gln
 76 Thr Tyr Val Asn Ile Gly Ile Ser Leu Ile Thr Leu Ala Val Pro
 91 Glu Ile Gly Ile Phe Leu Ser Leu Gly Pro Asn Ala Lys Asp Ala
106 Leu Asn Lys His Asp Pro Ala Pro Ile Pro Gln Ile Asp Arg Ile
121 Phe Ala Met Ala Met Lys Pro Ala Pro Gln Met Glu Ile Ser Gly
136 Leu Thr Ala Asp Glu Gln Ala Arg Gln Leu Asn Ser Gly Asp Ile
151 Leu Gln Asn Leu Ala Ala Arg Tyr Lys Val Ser Thr Met Ile Lys
166 Gln Ser His Gly Gly Phe Asn Lys Val Asp Met Asp Ser Ile Asp
181 Lys Phe Thr Asp Asp Val Ser Leu Ser Asn Thr Met Tyr Thr Asp
196 Arg Leu Pro Val Phe Ile Thr Asp Asn Thr Ala Asp Arg Thr Leu
```

Figure 3A

```
211 Leu Gly Leu Pro Tyr Tyr Ala Ile Leu Ala Ser Met His Leu Met
226 Leu Arg Asp Ile Ile Thr Lys Gly Pro Thr Trp Asp Ser Lys
241 Ile Asn Phe Thr Pro Asp Ala Ile Asp Ser Phe Lys Thr Asp Ile
256 Lys Asn Ile Lys Leu Tyr Ser Thr Ile Tyr Asp Val Phe
271 Gln Lys Gly Leu Ala Ser Tyr Gly Thr Pro Ser Asp Leu Glu Ser
286 Phe Ala Lys Lys Gln Lys Tyr Ile Glu Ile Met Thr Thr His Cys
301 Leu Asp Phe Ala Arg Leu Phe Pro Thr Phe Asp Pro Asp Leu Tyr
316 Pro Thr Gly Ser Gly Asp Ile Ser Leu Gln Lys Thr Arg Arg Ile
331 Leu Ser Pro Phe Ile Pro Ile Arg Thr Ala Asp Gly Leu Thr Leu
346 Asn Asn Thr Ser Ile Asp Thr Ser Asn Pro Lys Tyr Pro Asn Asn
361 Gly Asn Gly Ala Phe Pro Asn Pro Lys Gly Ala Arg Gln Ile Lys Gln
376 Phe Lys Leu Tyr Pro Ser Trp Arg Ala Gly Tyr Asp Gly Leu
391 Leu Gln Pro Tyr Leu Trp Ala Ile Glu Val Gln Asp Ser Val Glu
406 Thr Arg Leu Tyr Leu Pro Ala Val Asp Val Asp Pro Gln Ala Gly
421 Pro Asn Tyr Val Ser Ile Asp Ser Ser Asn Pro Ile Ile Gln Ile
```

Figure 3B

```
436 Asn Met Asp Thr Trp Lys Thr Pro Pro Gln Gly Ala Ser Gly Trp
451 Asn Thr Asn Leu Met Arg Gly Ser Val Ser Gly Leu Ser Phe Leu
466 Gln Arg Asp Gly Thr Arg Leu Ser Ala Gly Met Gly Gly Gly Phe
481 Ala Asp Thr Ile Tyr Ser Leu Pro Ala Thr His Tyr Leu Ser Tyr
496 Leu Tyr Gly Thr Pro Tyr Gln Thr Ser Asp Asn Tyr Ser Gly His
511 Val Gly Ala Leu Val Gly Val Ser Thr Pro Gln Glu Ala Thr Leu
526 Pro Asn Ile Ile Gly Gln Pro Asp Glu Gln Gly Asn Val Ser Thr
541 Met Gly Phe Pro Phe Glu Lys Ala Ser Tyr Gly Thr Val Pro Gly
556 Lys Glu Trp Leu Asn Gly Ala Asn Ala Met Lys Leu Ser Glu Tyr
571 Gln Ser Ile Gly Pro Ile Thr Asn Val Thr Ser Gly Gly Val Phe
586 Gln Ile Arg Cys Arg Tyr Ala Ser Asn Asp Asn Thr Asn Val Phe
601 Phe Asn Val Asp Thr Gly Gly Ala Asn Pro Ile Phe Gln Gln Ile
616 Asn Phe Ala Ser Thr Val Asp Asn Asn Thr Gly Val Gln Gly Ala
```

Figure 3C

```
631 Asn Gly Val Tyr Val Val Lys Ser Ile Ala Thr Thr Asp Asn Ser
646 Phe Thr Val Lys Ser Ile Pro Ala Lys Thr Ile Asn Val His Leu Thr
661 Asn Gln Gly Ser Ser Asp Val Phe Leu Thr Asp Arg Ile Glu Phe Val
676 Pro Ile Leu Glu Ser Asn Thr Val Thr Leu Ile Phe Asn Asn Ser Tyr
691 Thr Thr Gly Ser Ala Asn Leu Ile Pro Ala Ile Phe Ala Pro Leu Trp
706 Ser Thr Ser Ser Asp Lys Ala Leu Thr Gly Ser Met Ser Ile Thr
721 Gly Arg Thr Pro Asn Ser Asp Ala Leu Leu Arg Phe Phe
736 Lys Thr Asn Tyr Asp Thr Gln Thr Ile Pro Ile Pro Gly Ser Gly Ile
751 Lys Asp Phe Thr Asn Thr Leu Glu Ile Gln Asp Ile Val Ser Ile
766 Asp Ile Phe Val Gly Ser Gly Leu His Gly Ser Ser Asp Gly Ser Ile
781 Lys Leu Asp Phe Thr Asn Asn Ser Gly Ser Ser Ser Gly Gly Ser Pro
```

Figure 3D

| | | | | | | | | | | | | | | | |
|---|---|---|---|---|---|---|---|---|---|---|---|---|---|---|---|
| 796 | Lys | Ser | Phe | Thr | Glu | Gln | Asn | Asp | Leu | Glu | Asn | Ile | Thr | Thr | Gln |
| 811 | Val | Asn | Ala | Leu | Phe | Ser | Asn | Gln | Asp | Thr | Ala | Leu | Lys | Ala | Thr |
| 826 | Asp | Val | Ser | Asp | His | Asp | Ile | Glu | Val | Val | Leu | Lys | Val | Val | Asp |
| 841 | Ala | Leu | Ser | Asp | Glu | Val | Phe | Gly | Lys | Glu | Lys | Lys | Thr | Leu | Arg |
| 856 | Lys | Phe | Val | Asn | Gln | Ala | Lys | Arg | Leu | Ser | Ala | Arg | Arg | Asn | Leu |
| 871 | Leu | Val | Gly | Gly | Asn | Phe | Asp | Asn | Leu | Asp | Ala | Trp | Tyr | Arg | Gly |
| 886 | Arg | Asn | Val | Val | Ser | Asn | Ser | Asn | His | Glu | Leu | Leu | Lys | Ser | Asp |
| 901 | His | Val | Leu | Leu | Pro | Pro | Gly | Leu | Ser | Pro | Ser | Tyr | Ile | Phe |
| 916 | Gln | Lys | Val | Glu | Ile | Ser | Lys | Leu | Lys | Arg | Asn | Thr | Arg | Tyr | Thr |
| 931 | Val | Ser | Gly | Phe | Ala | His | Ile | Thr | Asp | Leu | Glu | Ile | Val | Val | Val |
| 946 | Ser | Arg | Tyr | Gly | Gln | Ile | Lys | Lys | Val | Gln | Val | Gln | Pro | Tyr |
| 961 | Gly | Glu | Ala | Phe | Gly | Thr | Ser | Ser | Gly | Pro | Val | Cys | Ile |
| 976 | Pro | His | Ser | Thr | Asn | Gly | Thr | Leu | Gly | Asn | Pro | His | Phe | Phe |
| 991 | Ser | Tyr | Ser | Ile | Asp | Val | Gly | Ala | Leu | Asp | Val | Thr | Asn | Pro |
| 1006 | Gly | Ile | Glu | Phe | Gly | Leu | Arg | Ile | Val | Asn | Pro | Thr | Gly | Met | Ala |

Figure 3E

```
1021 Arg Val Ser Asn Leu Glu Ile Arg Glu Asp Arg Pro Leu Ala Ala
1036 Asn Glu Ile Arg Gln Val Gln Arg Val Ala Arg Asn Trp Arg Thr
1051 Glu Tyr Glu Lys Glu Ala Glu Val Thr Ser Ile Leu Gln Pro
1066 Val Ile Asn Arg Ile Asn Gly Leu Tyr Asp Arg Asn Gly Asn Trp Asn
1081 Gly Ser Ile Arg Ser Asp Ile Ser Tyr Gln Asn Ile Asp Met Ala Ile
1096 Val Leu Pro Thr Leu Pro Lys Leu Arg His Trp Phe Met Ser Asp
1111 Arg Phe Ser Glu Gly Asp Ile Met Ala Lys Phe Gln Leu Gly Ala
1126 Leu Asn Arg Ala Tyr Ala Gln Leu Gln Asn Thr Leu Leu His
1141 Asn Gly His Phe Thr Lys Asp Ala Ala Asn Trp Thr Val Glu Gly
1156 Asp Ala His Gln Val Val Leu Glu Gly Lys Arg Arg Val Leu Arg
1171 Leu Pro Asp Trp Ser Ser Ser Val Ser Gln Thr Ile Ile Leu Glu
1186 Asn Phe Asp Pro Lys Tyr Gln Leu Val Phe His Gly Gln
1201 Gly Glu Gly Thr Val Thr Leu Gly Gly Glu Thr Thr Lys Tyr
1216 Ile Glu Thr His His His Phe Ala Asn Phe Thr Thr Ser Gln
1231 Arg Gln Gly Leu Thr Phe Glu Ser Asn Lys Val Thr Val Thr Ile
1246 Ser Ser Glu Asp Gly Leu Phe Glu Leu Val Asp Asn Ile Ala Leu Val
1261 Glu Ala Pro Leu Pro Thr Asp Asp Gln Asn Ser Glu Gly Asn Asn
1276 Ala Ser Ser Thr Asn Ser Asp Thr Ser Met Asn Asn Gln
```

Figure 3F

```
  1  ATGGCAATTT TAAATGAATT ATATCCATCT GTACCTTATA ATGTATTGGC
 51  GTATACGCCA CCCTCTTTTT TACCTGATGC GGGTACACAA GCTACACCTG
101  CTGACTTAAC AGCTTATGAA CAATTGTTGA AAAATTTAGA AAAAGGGATA
151  AATGCTGGAA CTTATTCGAA AGCAATAGCT GATGTACTTA AAGTATTTT
201  TATAGATGAT ACAATAAATT ATCAAACATA TGTAAATATT GGTTTAAGTT
251  TAATTACATT AGCTGTACCG GAAATTGGTA TTTTTACACC TTTCATCGGT
301  TTGTTTTTG CTGCATTGAA TAAACATGAT GCTCCACCTC CTCCTAATGC
351  AAAAGATATA TTTGAGGCTA TGAAACCAGC GATTCAAGAG ATGATTGATA
```

Figure 4A

```
401  GAACTTTAAC TGCGGATGAG CAAACATTTT TAAATGGGGA AATAAGTGGT
451  TTACAAAATT TAGCAGCAAG ATACCAGTCT ACAATGGATG ATATTCAAAG
501  CCATGGAGGA TTTAATAAGG TAGATTCTGG ATTAATTAAA AAGTTTACAG
551  ATGAGGTACT ATCTTTAAAT AGTTTTTATA CAGATCGTTT ACCTGTATTT
601  ATTACAGATA ATACAGCGGA TCGAACTTTG TTATGTTATT CTTATTATGC
651  TATACTTGCG AGCATGCATC TTAGTCTTC AAGAGATATC ATTACTAAGG
701  GTCCGACATG GGATTCTAAA ATTAATTCA CACCAGATGC AATTGATTCC
751  TTTAAACCG ATATTAAAAA TAATATAAAG CTTTACTCTA AAACTATTA
801  TGACGTATTT CAGAAGGGAC TTGCTTCATA CGGAACGCCT TCTGATTTAG
851  AGTCCTTTGC AAAAAAACAA AAATATATTG AAATTATGAC AACACATTGT
```

Figure 4B

```
 901  TTAGATTTTG CAAGATTGTT TCCTACTTTT GATCCAGATC TTTATCCAAC
 951  AGGATCAGGT GATATAAGTT TACAAAAAAC ACGTAGAATT CTTTCTCCTT
1001  TTATCCCTAT ACGTACTGCA GATGGGTTAA CATTAAATAA TACTTCAATT
1051  GATACTTCAA ATTGGCCTAA TTATGAAAAT GGGAATGGCG CGTTTCCAAA
1101  CCCAAAGAA AGAATATTAA AACAATTCAA ACTGTATCCT AGTTGGAGAG
1151  CGGGACAGTA CGGTGGGCTT TTACAACCTT ATTTATGGGC AATAGAAGTC
1201  CAAGATTCTG TAGAGACTCG TTTGTATGGG CAGCTTCCAG CTGTAGATCC
1251  ACAGGCAGGG CCTAATTATG TTTCCATAGA TTCTTCTAAT CCAATCATAC
1301  AAATAAATAT GGATACTTGG AAAACACCAC CACAAGGTGC GAGTGGGTGG
1351  AATACAAATT TAATGAGAGG AAGTGTAAGC GGGTTAAGTT TTTACAACG
```

Figure 4C

```
1401  AGATGGTACG AGACTTAGTG CTGGTATGGG TGGTGGTTTT GCTGATACAA
1451  TATATAGTCT CCCTGCAACT CATTATCTTT CTTATCTCTA TGGAACTCCT
1501  TATCAAACTT CTGATAACTA TTCTGGTCAC GTTGGTGCAT TGGTAGGTGT
1551  GAGTACGCCT CAAGAGGCTA CTCTTCCTAA TATTATAGGT CAACCAGATG
1601  AACAGGGAAA TGTATCTACA ATGGGATTTC CGTTTGAAAA AGCTTCTTAT
1651  GGAGGTACAG TTGTTAAAGA ATGGTTAAAT GGTGCGAATG CGATGAAGCT
1701  TTCTCCTGGG CAATCTATAG GTATTCCTAT TACAAATGTA ACAAGTGGAG
1751  AATATCAAAT TCGTTGTCGT TATGCAAGTA ATGATAATAC TAACGTTTTC
1801  TTTAATGTAG ATACTGGTGG AGCAAATCCA ATTTCCAAC  AGATAAACTT
```

Figure 4D

```
1851  TGCATCTACT GTAGATAATA ATACGGGAGT ACAAGGAGCA AATGGTGTCT
1901  ATGTAGTCAA ATCTATTGCT ACAACTGATA ATTCTTTTAC AGTAAAAATT
1951  CCTGCGAAGA CGATTAATGT TCATTAACC  AACCAAGGTT CTTCTGATGT
2001  CTTTTTAGAT CGTATTGAGT TTGTTCCAAT TCTAGAATCA AATACTGTAA
2051  CTATATTCAA CAATTCATAT ACTACAGGTT CAGCAAATCT TATACCAGCA
2101  ATAGCTCCTC TTTGGAGTAC TAGTTCAGAT AAAGCCCTTA CAGGTTCTAT
2151  GTCAATAACA GGTCGAACTA CCCCTAACAG TGATGATGCT TTGCTTCGAT
2201  TTTTTAAAAC TAATTATGAT ACACAAACCA TTCCTATTCC GGGTTCCGGA
2251  AAAGATTTTA CAAATACTCT AGAAATACAA GACATAGTTT CTATTGATAT
2301  TTTTGTCGGA TCTGGTCTAC ATGGATCCGA TGGATCTATA AAATTAGATT
```

Figure 4E

```
2351  TTACCAATAA  TAATAGTGGT  AGTGGTGGCT  CTCCAAAGAG  TTTCACCGAG
2401  CAAAATGATT  TAGAGAATAT  CACAACACAA  GTGAATGCTC  TATTCACATC
2451  TAATACACAA  GATGCACTTG  CAACAGATGT  GAGTGATCAT  GATATTGAAG
2501  AAGTGGTTCT  AAAAGTAGAT  GCATTATCTG  ATGAAGTGTT  TGGAAAAGAG
2551  AAAAAAACAT  TGCGTAAATT  TGTAAATCAA  GCGAAGCGCT  TAAGCAAGGC
2601  GCGTAATCTC  CTGGTAGGAG  GCAATTTTGA  TAACTTGGAT  GCTTGGTATA
2651  GAGGAAGAAA  TGTAGTAAAC  GTATCTAATC  ACGAACTGTT  GAAGAGTGAT
2701  CATGTATTAT  TACCACCACC  AGGATTGTCT  CCATCTTATA  TTTTCCAAAA
2751  AGTGGAGGAA  TCTAAATTAA  AACGAAATAC  ACGTTATACG  GTTTCTGGAT
2801  TTATTGCGCA  TGCAACAGAT  TTAGAAATTG  TGGTTTCTCG  TTATGGGCAA
```

Figure 4F

```
2851  GAAATAAAGA AAGTGGTGCA AGTTCCTTAT GGAGAAGCAT TCCCATTAAC
2901  ATCAAGTGGA CCAGTTTGTT GTATCCCACA TTCTACAAGT AATGGAACTT
2951  TAGGCAATCC ACATTTCTTT AGTTACAGTA TTGATGTAGG TGCATTAGAT
3001  GTAGACACAA ACCCTGGTAT TGAATTCGGT CTTCGTATTG TAAATCCAAC
3051  TGGAATGGCA CGCGTAAGCA ATTTGGAAAT TCGTGAAGAT CGTCCATTAG
3101  CAGCAAATGA AATACGACAA GTACAACGTG TCGCAAGAAA TTGGAGAACC
3151  GAGTATGAGA AAGAACGTGC GGAAGTAACA AGTTAATTC AACCTGTTAT
3201  CAATCGAATC AATGGATTGT ATGACAATGG AAATTGGAAC GGTTCTATTC
3251  GTTCAGATAT TTCGTATCAG AATATAGACG CGATTGTATT ACCAACGTTA
```

Figure 4G

```
3301  CCAAGTTAC  GCCATTGGTT  TATGTCAGAT  AGATTAGTG   AACAAGGAGA
3351  TATCATGGCT  AAATTCCAAG  GTGCATTAAA  TCGTGCGTAT  GCACAACTGG
3401  AACAAAATAC  GCTTCTGCAT  AATGGTCATT  TTACAAAAGA  TGCAGCCAAT
3451  TGGACGGTAG  AAGGCGATGC  ACATCAGGTA  GTATTAGAAG  ATGGTAAACG
3501  TGTATTACGA  GGTCTTCGAG  AAAGAATATC  TGTGTCTCAA  ACGATTGAAA
3551  TCGAGAATTT  TGATCCAGAT  AAAGAATATC  AATTAGTATT  TCATGGGCAA
3601  GGAGAAGGAA  CGGTTACGTT  GGAGCATGGA  GAAGAAACAA  AATATATAGA
```

Figure 4H

```
3651  AACGCATACA CATCATTTTG CGAATTTTAC AACTTCTCAA CGTCAAGGAC
3701  TCACGTTTGA ATCAAATAAA GTGACAGTGA CCATTCTTC AGAAGATGGA
3751  GAATTCTTAG TGGATAATAT TGCGCTTGTA GAAGCTCCTC TTCCTACAGA
3801  TGACCAAAAT TCTGAGGGAA ATACGGCTTC CAGTACGAAT AGGGATACAA
3851  GTATGAACAA CAATCAA*
```

Figure 4I

GENES ENCODING NEMATODE-ACTIVE TOXINS CLONED FROM *BACILLUS THURINGIENSIS* ISOLATE PS17

CROSS-REFERENCE TO A RELATED APPLICATION

This is a continuation-in-part of co-pending application Ser. No. 535,810, filed Jun. 11, 1994, now abandoned, which is a continuation-in-part of co-pending application Ser. No. 084,653, filed on Aug. 12, 1987, now U.S. Pat. No. 4,948,734.

BACKGROUND OF THE INVENTION

Regular use of chemicals to control unwanted organisms can select for drug resistant strains. This has occurred in many species of economically important insects and has also occurred in nematodes of sheep, goats, and horses. The development of drug resistance necessitates a continuing search for new control agents having different modes of action.

In recent times, the accepted methodology for control of nematodes has centered around the drug benzimidazole and its congeners. The use of these drugs on a wide scale has led to many instances of resistance among nematode populations (Prichard, R. K. et al. [1980] "The problem of anthelmintic resistance in nematodes," Austr. Vet. J. 56:239-251; Coles, G. C. [1986] "Anthelmintic resistance in sheep," In *Veterinary Clinics of North America: Food Animal Practice*, Vol 2:423-432 [Herd, R. P., eds.] W. B. Saunders, New York). There are more than 100,000 described species of nematodes.

The bacterium *Bacillus thuringiensis* (Bt.) produces a δ-endotoxin polypeptide that has been shown to have activity against a rapidly growing number of insect species. The earlier observations of toxicity only against lepidopteran insects have been expanded with descriptions of B.t. isolates with toxicity to dipteran and coleopteran insects. These toxins are deposited as crystalline inclusions within the organism. Many strains of B.t. produce crystalline inclusions with no demonstrated toxicity to any insect tested.

A small number of research articles have been published about the effects of delta endotoxins from *B. thuringiensis* species on the viability of nematode eggs. Bottjer, Bone and Gill (Experimental Parasitology 60:239-244, 1985) have reported that *B.t. kurstaki* and *B.t. israelensis* were toxic in vitro to eggs of the nematode *Trichostrongylus colubriformis*. In addition, 28 other B.t. strains were tested with widely variable toxicities. The most potent had LD$_{50}$ values in the nanogam range. Ipoffo and Dropkin (Ignoffo, C. M. and Dropldn, V. H. [1977] J. Kans. Entomol. Soc. 50:394-398) have reported that the thermostable toxin from *Bacillus thuringiensis* (beta exotoxin) was active against a free-living nematode, *Panagrellus redivivus* (Goodey); a plant-parasitic nematode, *Meloidogyne incognita* (Chitwood); and a fungus-feeding nematode, *Aphelenchus avena* (Bastien). Beta exotoxin is a generalized cytotoxic agent with little or no specificity. Also, H. Ciordia and W. E. Bizzell (Jour. of Parasitology 47:41 [abstract] 1961) gave a preliminary report on the effects of *B. thuringiensis* on some cattle nematodes.

At the present time there is a need to have more effective means to control the many nematodes that cause considerable damage to susceptible hosts. Advantageously, such, effective means would employ biological agents. In parent pending application Ser. No. 084,653, there are disclosed novel isolates of *Bacillus thuringiensis* having activity against nematodes. We have now isolated, unexpectedly and advantageously, four genes encoding novel nematicidal δ-endotoxins from one of the B.t. isolates which was named B.t. PS17. Prior to successfully completing this invention, we could not predict with any reasonable degree of certainty that we could isolate a gene encoding a nematicidal toxin because of the complexity of the microbial genome. The fact that more than one gene was successfully cloned is completely unexpected.

BRIEF SUMMARY OF THE INVENTION

The subject invention concerns four genes cloned from a novel *Bacillus thuringiensis* isolate designated B.t. PS17. The genes designated PS17d, PS17b, PS17a and PS17e, encode *Bacillus thuringiensis* δ-endotoxins which have nematicidal activity. The genes can be transferred to suitable hosts via a recombinant DNA vector.

BRIEF DESCRIPTION OF THE DRAWINGS

FIG. 1A-1E discloses the amino acid sequence of the novel toxin encoded by PS17a.

FIG. 2A-2F discloses the DNA of PS17a.

FIG. 3A-3F discloses the amino acid sequence of the novel toxin encoded by PS17b.

FIG. 4A-4I discloses the DNA of PS17b.

DETAILED DESCRIPTION OF THE INVENTION

The novel toxin genes of the subject invention were obtained from a nematode-active *B. thuringiensis* (Bt.) isolate designated PS17. A subculture of B.t. PS17 and the *E. coli* host harboring the toxin genes of the invention were deposited in the permanent collection of the Northern Research Laboratory, U.S. Department of Agriculture, Peoria, Ill., USA The accession numbers are as follows:

B.t. PS17 - NRRL B-18243 - Deposited on Jul. 28, 1987.

*E. coli* NM522(pMYC1627)—NRRL B-18651—Deposited on May 11, 1990.

*E. coli* NM522(pMYC1628)—NRRL B-18652—Deposited on May 11, 1990.

The subject cultures have been deposited under conditions that assure that access to the cultures will be available during the pendency of this patent application to one determined by the Commissioner of Patents and Trademarks to be entitled thereto under 37 CFR 1.14 and 35 USC 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposit, and in any case, for a period of at least 30 (thirty) years after the date of deposit or for the enforceable life of any patent which may issue disclosing the cultures. The depositor acknowledges the duty to replace the deposits should the depository be unable to furnish a sample when requested, due to the condition of the deposit(s). All restrictions on the availability to the public of the subject culture deposits wt be irrevocably removed upon the granting of a patent disclosing them.

The novel B.t. genes of the invention encode toxins which show activity against tested nematodes. The group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats and poultry. Among the helminths, the group of worms described as nematodes causes wide-spread and often times serious infection in various species of animals. The most common genera of nematodes infecting the animals referred to above are Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris, Caenorhabditis and Parascaris. Certain of these, such as Nematodirus, Cooperia, and Oesophagostomum, attack primarily the intestinal tract, while others, such as Dictyocaulus are found in the lungs. Still other parasites may be located in other tissues and organs of the body.

The to)dns encoded by the novel B.t. genes of the invention are useful as nematocides for the control of soil nematodes and plant parasites selected from the genera Bursaphalenchus, Criconemella, Ditylenchus, Globodera, Helicotylenchus, Heterodera, Melodiogyne, Pratylenchus, Radolpholus, Rotelynchus, or Tylenchus.

Alternatively, because some plant parasitic nematodes are obligate parasites, genes coding for nematocidal B.t. toxins can be engineered into plant cells to yield nematode-resistant plants. The methodology for engineering plant cells is well established (cf. Nester, E. W., Gordon, M. P., Amasino, R. M. and Yanofsky, M. F., Ann. Rev. Plant Physiol. 35:387-399, 1984).

The B.t. toxins of the invention can be administered orally in a unit dosage form such as a capsule, bolus or tablet, or as a liquid drench when used as an anthelmintic in mammals. The drench is normally a solution, suspension or dispersion of the active ingredient, usually in water, together with a suspending agent such as bentonite and a wetting agent or hke excipient. Generally, the drenches also contain an antifoaming agent. Drench formulations generally contain from about 0.001 to 0.5% by weight of the active compound. Preferred drench formulations may contain from 0.01 to 0.1% by weight, the capsules and boluses comprise the active ingredient admixed with a carrier vehicle such as starch, talc, napesium stearate, or dicalcium phosphate.

Where it is desired to administer the toxin compounds in a dry, solid unit dosage form, capsules, boluses or tablets containing the desired amount of active compound usually are employed. These dosage forms are prepared by intimately and uniformly mixing the active ingredient with suitable finely divided diluents, fillers, disintegrating agents and/or binders such as starch, lactose, talc, magnesium stearate, vegetable gums and the like. Such unit dosage formulations may be varied widely with respect to their total weight and content of the antiparasitic agent, depending upon the factors such as the type of host animal to be treated, the severity and type of infection and the weight of the host.

When the active compound is to be administered via an animal feedstuff, it is intimately dispersed in the feed or used as a top dressing or in the form of pellets which may then be added to the finished feed or, optionany, fed separately. Alternatively, the antiparasitic compounds may be administered to animals parenterally, for example, by intraruminal, intramuscular, intratracheal, or subcutaneous injection, in which event the active ingredient is dissolved or dispersed in a Equid carrier vehicle. For parenteral administration, the active material is suitably admixed with an acceptable vehicle, preferably of the vegetable oil variety, such as peanut oil, cotton seed oil and the hke. Other parenteral vehicles, such as organic preparations using solketal, glycerol, formal and aqueous parenteral formulations, are also used. The active compound or compounds are dissolved or suspended in the parenteral formulation for administration; such formulations generally contain from 0.005 to 5% by weight of the active compound.

When the toxins are administered as a component of the feed of the animals, or dissolved or suspended in the drinking water, compositions are provided in which the active compound or compounds are intimately dispersed in an inert carrier or diluent. By inert carrier is meant one that will not react with the antiparasitic agent and one that may be administered safely to animals. Preferably, a carrier for feed administration is one that is, or may be, an ingredient of the animal ration.

Suitable compositions include feed premixes or supplements in which the active ingredient is present in relatively large amounts and which are suitable for direct feeding to the animal or for addition to the feed either directly or after an intermediate dilution or blending step. Typical carriers or diluents suitable for such compositions include, for example, distiers' dried grains, corn meal, citrus meal, fermentation residues, ground oyster shells, wheat shorts, molasses solubles, corn cob meal, edible bean mill feed, soya grits, crushed limestone and the like.

The toxin genes of the subject invention can be introduced into a wide variety of microbial hosts. Expression of the toxin gene results, directly or indirectly, in the intracellular production and maintenance of the nematicide. With suitable hosts, e.g., Pseudomonas, the microbes can be applied to the situs of nematodes where they wt proliferate and be ingested by the nematodes. The result is a control of the nematodes. Alternatively, the microbe hosting the toxin gene can be treated under conditions that prolong the activity of the toxin produced in the cell. The treated ceil then can be applied to the environment of target pest(s). The resulting product retains the toidcity of the B.t. toxin.

Where the B.t. toxin gene is introduced via a suitable vector into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the nematicide from environmental degradation and inactivation.

A large number of microorganisms are known to inhabit the phylloplane (the surface of the plant leaves)

and/or the rhizosphere (the soil surrounding plant roots) of a wide variety of important crops. These microorganisms include bacteria, algae, and fungi. Of particular interest are microorganisms, such as bacteria, e.g., genera Pseudomonas, Erwinia, Serratia, Klebsiella, Xanthomonas, Streptomyces, Rhizobium, Rhodopseudomonas, Methylophilius, Agrobacterium, Acetobacter, Lactobacillus, Arthrobacter, Azotobacter, Leuconostoc, and Alcaligenes, fungi, particularly yeast, e.g., genera Saccharomyces, Cryptococcus, Kluyveromyces, Sporobolomyces, Rhodotorula and Aureobasidium. Of particular interest are such phytosphere bacterial species as Pseudomonas syringae. Pseudomonas fluorescens, Serratia marcescens, Acetobacter xylinum, Agrobacterium tumefaciens, Rhodopseudomonas spheroides, Xanthomonas campestris, Rhizobium melioti, Alcaligenes entrophus, and Azotobacter vinlandii; and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae,* and *Aureobasidium pollulans*. Of particular interest are the pigmented microorganisms.

A wide variety of ways are known and available for introducing the B.t. genes expressing the toxin into the microorganism host under conditions which allow for stable maintenance and expression of the gene. The transformants can be isolated in accordance with conventional ways, usually employing a selection technique, which allows for selection of the desired organism as against unmodified organisms or transferring organisms, when present. The transformants then can be tested for nematicidal activity.

Suitable host cells, where the nematicide-containing cells will be treated to prolong the activity of the toxin in the cell when the then treated cell is applied to the environment of target pest(s), may include either prokaryotes or eukaryotes, normally being limited to those cells which do not produce substances to)dc to higher organisms, such as mammals. However, organisms which produce substances to)dc to higher organisms could be used, where the toxin is unstable or the level of application sufficiently low as to avoid any possibility of toxicity to a mammalian host. As hosts, of particular interest wt be the prokaryotes and the lower eukaryotes, such as fungi. Mustrative prokaryotes, both Gram-negative and—positive, include Enterobacteriaceae, such as Escherichia, *Erwinia, Shigella,* Salmonella, and Proteus; Bacillaceae; Rhizobiceae, such as Rhizobium; Spirillaceae, such as photobacterium, Zymomonas, Serratia, Aeromonas, Vibrio, Desulfovibrio, Spirillum, Lactobacillaceae; Pseudomonadaceae, such as Pseudomonas and Acetobacter; Azotobacteraceae and Nitrobacteraceae. Among eukaryotes are fungi, such as Phycomycetes and Ascomycetes, which includes yeast, such as Saccharomyces and Schizosaccharomyces; and Basidiomycetes yeast, such as Rhodotorula, Aureobasidium, Sporobolomyces, and the like.

Characteristics of particular interest in selecting a host cell for purposes of production include ease of introducing the B.t. gene into the host, availability of expression systems, efficiency of expression, stability of the nematicide in the host, and the presence of auxiliary genetic capabilities. Characteristics of interest for use as a nematicide microcapsule include protective qualities for the nematicide, such as thick cell walls, pigmentation, and intracellular packaging or formation of inclusion bodies; leaf affinity; lack of mammalian toxicity; attractiveness to pests for ingestion; ease of kileng and fixing without damage to the toxin; and the like. Other considerations include ease of formulation and handling, economics, storage stability, and the like.

Host organisms of particular interest include yeast, such as Rhodotorula sp., Aureobasidium sp., Saccharomyces sp., and Sporobolomyces sp.; phylloplane organisms such as Pseudomonas sp., Erwinia sp. and Flavobacterium sp.; or such other organisms as Escherichia, Lactobacillus sp., Bacillus sp., and the like. Specific organisms include *Pseudomonas aeruginosa, Pseudomonas fluorescens, Saccharomyces cerevisiae, Bacillus thuringiensis, Escherichia coli, Bacillus subtilis,* and the like.

The cell wt usually be intact and be substantially in the proliferative form when treated, rather than in a spore form, although in some instances spores may be employed.

Treatment of the microbial cell, e.g., a microbe containing the B.t. toxin gene, can be by chemical or physical means, or by a combination of chemical and/or physical means, so long as the technique does not deleteriously affect the properties of the toxin, nor diminish the cellular capability in protecting the toxin. Examples of chemical reagents are halogenating agents, particularly halogens of atomic no. 17-80. More particularly, iodine can be used under mild conditions and for sufficient time to achieve the desired results. Other suitable techniques include treatment with aldehydes, such as formaldehyde and glutaraldehyde; anti-infectives, such as zephiran chloride and cetylpyridinium chloride; alcohols, such as isopropyl and ethanol; various histologic fixatives, such as Bouin's fixative and Helly's fixative (See: Humason, Gretchen L., Animal Tissue Techniques, W. H. Freeman and Company, 1967); or a combination of physical (heat) and chemical agents that preserve and prolong the activity of the toxin produced in the cell when the cell is administered to the host animal. Examples of physical means are short wavelength radiation such as gamma-radiation and X-radiation, freezing, UV irradiation, lyophilization, and the like.

The ceils generally will have enhanced structural stability which will enhance resistance to environmental conditions. Where the pesticide is in a proform, the method of inactivation should be selected so as not to inhibit processing of the proform to the mature form of the pesticide by the target pest pathogen. For example, formaldehyde will crosslink proteins and could inhibit processing of the proform of a polypeptide pesticide. The method of inactivation or killing retains at least a substantial portion of the bio-availability or bioactivity of the toxin.

The cellular host containing the B.t. nematicidal gene may be grown in any convenient nutrient medium, where the DNA construct provides a selective advantage, providing for a selective medium so that substantially au or an of the ceils retain the B.t. gene. These cells may then be harvested in accordance with conventional ways. Alteratively, the cells can be treated prior to harvesting.

The B.t. cells may be formulated in a variety of ways. They may be employed as wettable powders, granules or dusts, by mixing with various inert materials, such as inorganic minerals (phyllosilicates, carbonates, sulfates, phosphates, and the like) or botanical materials (powdered comcobs, rice hues, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rheological agents, surfactants, emulsifiers, dispersants, or polymers.

The nematicide concentration wt vary widely depending upon the nature of the particular formulation, particularly whether it is a concentrate or to be used directly. The nematicide will be present in at least 1% by weight and may be 100% by weight. The dry formulations will have from about 1-95% by weight of the nematicide while the liquid formulations wt generally be from about 1-60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the nematodes, e.g., plants, soil or water, by spraying, dusting, sprinkling, or the like.

Following are examples which frustrate procedures, including the best mode, for practicing the invention. These examples should not be construed as limiting. All percentages are by weight and all solvent mixture proportions are by volume unless otherwise noted.

EXAMPLE 1

Culturing B.t. PS17, NRRL B-18243

A subculture of B.t. PS17, NRRL B-18243, can be used to inoculate the following medium, a peptone, glucose, salts medium.

| | |
|---|---|
| Bacto Peptone | 7.5 g/l |
| Glucose | 1.0 g/l |
| KH$_2$PO$_4$ | 3.4 g/l |
| K$_2$HPO$_4$ | 4.35 g/l |
| Salt Solution | 5.0 ml/l |
| CaCl$_2$ Solution | 5.0 ml/l |
| Salts Solution (100 ml) | |
| MgSO$_4$.7H$_2$O | 2.46 g |
| MnSO$_4$.H$_2$O | 0.04 g |
| ZnSO$_4$.7H$_2$O | 0.28 g |
| FeSO$_4$.7H$_2$O | 0.40 g |
| CaCl$_2$ Solution (100 ml) | |
| CaCl$_2$.2H$_2$O | 3.66 g |
| pH 7.2 | |

The salts solution and CaCl$_2$ solution are filter-sterilized and added to the autoclaved and cooked broth at the time of inoculation. Flasks are incubated at 30° C. on a rotary shaker at 200 rpm for 64 hr.

EXAMPLE 2

Purification and N-Terminal Sequencing of Bt. Isolate PS17

The *Bacillus thuringiensis* (Bt.) isolate used as the source of nematicidal toxin protein of the subject invention is identified as B.t. strain PS17. The culture was grown using standard media and fermentation techniques well known in the art. The toxin protein inclusions were harvested by standard sedimentation centrifugation. The recovered protein inclusions were partially purified by sodium bromide (28-38%) isopycnic gradient centrifugation (Pfannenstiel, M. A, E. J. Ross, V. C. Kramer, and K. W. Nickerson [1984] FEMS Microbioi. Lett. 21:39). Thereafter the individual toxin proteins were resolved by solubilffing the crystalline protein complex in an alkah buffer and fractionating the individual proteins by DEAE-sepharose CL-6B (Sigma Chem. Co., St. Louis, Mo.) chromatography by stepwise increments of increasing concentrations of an NaCl-containing buffer (Reichenberg, D., in Ion Exchangers in Organic and Biochemistly [C. Calmon and T. R. E. Kressman, eds.], Interscience, New York, 1957). Fractions containing protein toxic for the nematode *Caenorhabditis elegans* (CE), were bound to PVDF membrane (Millipore, Bedford, Mass.) by western blotting techniques (Towbin, H., T. Staehelin, and IC Gordon [1979] Proc. Natl. Acad. Sci. USA 76:4350) and the N-terminal amino acids were determined by the standard Edman reaction with an automated gas-phase sequenator (Hunkapffler, M. W., R. M. Hewick, W. L. Dreyer, and L. E. Hood [1983] Meth. Enzymol. 91:399). From these sequence data an oligonucleotide probe was designed by utilizing a codon frequency table assembled from available nucleotide sequence data of other B.t. toxin genes. The probe was synthesized on an Applied Biosystems, Inc. DNA synthesis machine.

The above procedure can be readily scaled up to large fermentors by procedures well known in the art.

The B.t. spores and/or crystals, obtained in the above fermentation, can be isolated by procedures well known in the art. A frequently-used procedure is to subject the harvested fermentation broth to separation techniques, e.g., centrifugation.

EXAMPLE 3

Cloning of Four Novel Toxin Genes from B.t. PS17 and Transformation into *Escherichia coli*

Total cellular DNA was prepared by growing the cells B.t. PS17 to a low optical density (OD$_{600}$=1.0) and recovering the ceils by centrifugation. The cells were protoplasted in TES buffer (30 mM Tris-Cl, 10 mM EDTA, 50 mM NaCl, pH =8.0) containing 20 % sucrose and 50 mg/ml lysozyme. The protoplasts were lysed by addition of SDS to a final concentration of 4%. The cellular material was precipitated overnight at 4° C. in 100 mM (final concentration) neutral potassium chloride. The supermate was extracted twice with phenol/chloroform (1:1). The DNA was precipitated with ethanol and purified by isopycnic banding on a cesium chloride-ethidium bromide gradient.

Total cellular DNA from PS17 was digested with EcoRI and separated by electrophoresis on a 0.8% (w/v) Agarose-TAE (50mm Tris-HCI, 20mM NaOAc, 2.5mM EDTA, pH=8.0) buffered gel. A Southern blot of the gel was hybridized with a [$^{32}$p]—radiolabeled ohgonucleotide probe derived from the N-terminal amino acid sequence of purified 130kDa protein from PS17. The sequence of the oligonucleotide synthesized is (GCAATMAAATGAATTATATCC). Results showed that the hybridizing EcoRI fragments of PS17 are 5.Okb, 4.5kb, 2.7kb and 1.8kb in size, presumptively identifying at least four new nematode-active toxin genes, PS17d, PS17b, PS17a and PS17e, respectively.

A library was constructed from PS17 total cellular DNA partially digested with Sau3A and size fractionated by electrophoresis. The 9 to 23kb region of the gel was excised and the DNA was electroeluted and then concentrated using an Elutip$^{TM}$ ion exchange colurim (Schleicher and Schuel, Keene NH). The isolated Sau3A fragments were ligated into LambdaGEM-11 $^{TM}$ (PROMEGA). The packaged phage were plated on KW251 E. coli cells(PROMF-GA) at a high titer and screened using the above radiolabeled synthetic oligonucleotide as a nucleic acid hybridization probe. Hybridizing plaques were purified and rescreened at a lower plaque density. Single isolated purified plaques that hybridized vath the probe were used to infect KW251 E. coli cells in liquid culture for preparation of phage for DNA isolation. DNA was isolated by standard procedures.

Recovered recombinant phage DNA was digested with EcoRI and separated by electrophoresis on a 0.8% agarose-TAE gel. The gel was Southern blotted and hybridized with the oligonucleotide probe to characterize the toxin genes isolated from the lambda library. Two patterns were present, clones containing the 4.5kb (PS17b) or the 2.7kb (PS17a) EcoRI fragments. Preparative amounts of phage DNA were digested with SalI (to release the inserted DNA from lambda arms) and separated by electrophoresis on a 0.6% agarose-TAE gel. The large fragments, electroeluted and concentrated as described above, were legated to SalI-digested and dephosphorylated pBClac. The hgation mix was introduced by transformation into NM522 competent E. coli cells and plated on LB agar containing ampicirin, isopropyl-(Beta)-D-thiogalactoside (IPTG) and 5-Bromo-4-Chloro-3-indolyl-(Beta)-D-galactoside(X-GAL). Mute colonies, with putative insertions in the (Beta)-galactosidase gene of pBClac, were subjected to standard rapid plasmed purification procedures to isolate the desired plasmeds. The selected plasmed containing the 2.7kb EcoRI fragment was named pMYC1627 and the plasmed containing the 4.5kb EcoRI fragment was called pNffC1628.

The toxin genes were sequenced by the standard Sanger dideoxy chain termination method using the synthetic oligonucleotide probe, disclosed above, and by "walking" with primers made to the sequence of the new toxin genes.

The vanous methods employed in the preparation of the plasmeds and transformation of host organisms are well known in the art. These procedures are all described in Maniatis, T., Fritsch, E. F., and Sambrook, J. (1982) *Molecular Cloning: A Laboratory Manual*, Cold Spring Harbor Laboratory, New York. Thus, it is within the skill of those in the genetic engineering art to extract DNA from microbial cells, perform restriction enzyme digestions, electrophorese DNA fragments, tail and anneal plasmed and insert DNA, ligate DNA, transform cees, prepare plasmed DNA, electrophorese proteins, and sequence DNA.

The restriction enzymes disclosed herein can be purchased from Bethesda Research Laboratories, Gaithersburg, Md., or New England Biolabs, Beverly, Mass. The enzymes are used according to the instructions provided by the supplier.

The PS17 toxin genes were subcloned into the shuttle vector pHT3101 (Lereclus, D. et al.[1989] FEMS Microbiol. Lett. 60:211-218) using standard methods for expression in B.t.. Briefly, SalI fragments containing the PS17b and a toxin genes were isolated from pMYC1627 and pMYC1628, respectively, by preparative agarose gel electrophoresis, electroelution, and concentrated, as described above. These concentrated fragments were ligated into SalI-cleaved and phosphatased pHT3101. The legation mixtures were used separately to transform frozen, competent *E. coli* NM522. Plasrnids from each respective recombinant E. coli strain were prepared by alkaline lysis and analyzed by agarose gel electrophoresis. The resulting subclones, pNffC2311 and pNffC2309, harbored the PS17a and b toxin genes, respectively. These plasmeds were transformed into the acrystaflfferous B.t. strain, HD-1 MB (Purdue University, Lafayette, Ind.), by standard electroporation techniques (Instruction Manual, Biorad, Richmond, Calif.).

Recombinant B.t. strains HD-1 gall [pMYC2311] and [pMYC2309] were grown to sporulation and the proteins purified by NaBr gradient centrifugation as described above for the wild-type B.t. proteins.

EXAMPLE 4

Actively of the B.t. Toxin Protein and Gene Product Against *Caenorhabditis elegans*

*Caenorhabditis elegans* (CE) was cultured as described by Simpkin and Coles (J. Chem. Tech. Biotechnol. 31:66-69, 1981) in coming (Coming Glass Works, Coming, N.Y.) 24-weH tissue culture plates containing 1ml S-basal media, 0.5mg ampicillin and 0.01 mg cholesterol. Each well also contained ca. $10^8$ cells of *Escherichia coli* strain OP-50, a uracfl auxotroph. The wells were seeded with ca. 100-200 CE per well and incubated at 20° C. Samples of protein (obtained from the wild type B.t. or the recombinant B.t.) were added to the wells by serial dilution. Water served as the control as well as the vehicle to introduce the proteins to the wells.

Each of the wells were examined daily and representative results are as follows:

| | % KILL | | |
|---|---|---|---|
| μg toxin | pMYC2309 | pMYC2311 | PS17 |
| 100 | 25 | 50 | 75 |
| 32 | 25 | 50 | 75 |
| 10 | 50 | 25 | 50 |
| 1 | 0 | 0 | 0 |

EXAMPLE 5

Activity Against the Plant Nematodes Pratylenchus spp.

The toxin encoded by Bt. PS17a has been found to be active against Pratylenchus spp. The activity is approximately at the same level as is disclosed in Example 4 against *C. elegans*.

Species of Pratylenchus, for example, *P. scribneri* and *P. redivivous*, are known pathogens of many economically important crops including corn, peanuts, soybean, alfalfa, beans, tomato, and citrus. These "root lesion" nematodes are the second most economically damagging genus of plant parasitic nematodes (after Meliodogyne—the "root knot" nematode), and typify the migratory endoparasites.

It is well known in the art that the amino acid sequence of a protein is determined by the nucleotide sequence of the DNA Because of the redundancy of the genetic code, i.e., more than one coding nucleotide triplet (codon) can be used for most of the amino acids used to make proteins, different nucleotide sequences can code for a particular amino acid. Thus, the genetic code can be depicted as follows:

| | | | |
|---|---|---|---|
| Phenylalanine (Phe) | TTK | Histidine (His) | CAK |
| Leucine (Leu) | XTY | Glutamine (Gln) | CAJ |
| Isoleucine (Ile) | ATM | Asparagine (Asn) | AAK |
| Methionine (Met) | ATG | Lysine (Lys) | AAJ |
| Valine (Val) | GTL | Aspartic acid (Asp) | GAK |
| Serine (Ser) | QRS | Glutamic acid (Glu) | GAJ |
| Proline (Pro) | CCL | Cysteine (Cys) | TGK |

| -continued | | | |
|---|---|---|---|
| Threonine (Thr) | ACL | Tryptophan (Trp) | TGG |
| Alanine (Ala) | GCL | Arginine (Arg) | WGZ |
| Tyrosine (Tyr) | TAK | Glycine (Gly) | GGL |
| Termination signal | TAJ | | |

Key: Each 3-letter deoxynucleotide triplet corresponds to a trinucleotide of mRNA, having a 5'-end on the left and a 3'-end on the right. AH DNA sequences given herein are those of the strand whose sequence correspond to the MRNA sequence, with thymine substituted for uracil. The letters stand for the purine or pyrimidine bases forming the deoxynucleotide sequence.

A=adenine
G=guanine
C=cytosine
T=thymine
X=T or C if Y is A or G
X=C if Y is C or T
Y=A, G, C or T if X is C
Y=A or G if X is T
W=C or A if Z is A or G
W-C if Z is C or T
Z=A, G, C or T ff W is C
Z=A or G if W is A
QR=TC if S is A, G, C or T; alteratively QR=AG if S is T or C
J=A or G
K=T or C
L=A, T, ℭ or G
M=A, C or T The above shows that the novel amino acid sequence of the B.t. toxins can be prepared by equivalent nucleotide sequences encoding the same amino acid sequence of the protein. Accordingly, the subject invention includes such equivalent nucleotide sequences. In addition it has been shown that proteins of identified structure and function may be constructed by changing the amino acid sequence if such changes do not alter the protein secondary structure (Kaiser, E. T. and Kezdy, F. J. [1984] Science 223:249-255). Thus, the subject invention includes mutants of the amino acid sequence depicted herein which do not alter the protein secondary structure, or if the structure is altered, the biological activity is substantially retained. Further, the invention also includes mutants of organisms hosting aB or part of a toxin encoding a gene of the invention. Such microbial mutants can be made by techniques well known to persons skilled in the art. For example, UV irradiation can be used to prepare mutants of host organisms. Likewise, such mutants may include asporogenous host cells which also can be prepared by procedures well known in the art.

We claim:

1. Isolated polynucleotide encoding a *Bacillus thuringiensis* nematicidal toxin having an amino acid sequence shown in FIG. 1A-1E.

2. Isolated polynucleotide encoding a *Bacillus thuringiensis* nematicidal toxin, said DNA having a nucleotide sequence shown in FIG. 2A-2F.

3. A recombinant DNA transfer vector comprising a gene designated B.t. PS17a.

4. The recombinant DNA transfer vector, according to claim 3, which comprises the nucleotide sequence which codes for an amino acid sequence shown in FIG. 1A-1E.

5. The vector comprising DNA, according to claim 17, wherein said DNA has the sequence shown in FIG. 2A-2F.

6. A recombinant DNA transfer vector, according to claim 3, designated pMYC1627.

7. A bacterial host transformed to express a *Bacillus thuringiensis* nematicidal toxin having the amino acid sequence shown in FIG. 1A-1E.

8. The bacterial host, according to claim 7, transformed to express a *Bacillus thuringiensis* nematicidal toxin encoded by a gene designated B.t. PS17a.

9. The transformed bacterial host, according to claim 7, wherein said nematicidal toxin having an amino acid sequence shown in FIG. 1A-1E, is encoded by DNA having a nucleotide sequence shown in FIG. 2.

10. Escherichia coli transformed with a plasmid vector containing a *Bacillus thuringiensis* nematicidal toxin gene encoding a Bacillus thuringiensis nematicidal toxin having an amino acid sequence shown in FIG. 1A-1E.

11. *Escherichia coli* (NM522)(pMYC1627), having the identifying characteristics of NRRL B-18651, according to claim 7.

12. A prokaryotic or eukaryotic microorganism or plant cell host transformed by the transfer vector of claim 3.

13. A prokaryotic or eukaryotic microorganism or plant cell host transformed by the transfer vector of claim 4.

14. A microorganism according to claim 13, which is a species of Pseudomonas, Azotobacter, Erwinia, Serratia, Klebsiella, Rhizobium, Rhodopseudomonas, Methylophilius, Agrobacterium, Acetobacter, Alcaligenes, Bacillus, or Streptomyces.

15. A microorganism according to claim 14, wherein said microorganism is pigmented and phylloplane adherent.

* * * * *

UNITED STATES PATENT AND TRADEMARK OFFICE
CERTIFICATE OF CORRECTION

PATENT NO. : 5,281,530

DATED : January 25, 1994

INVENTOR(S) : August J. Sick, George E. Schwab and Jewel Payne

It is certified that error appears in the above-indentified patent and that said Letters Patent is hereby corrected as shown below:

Column 1, line 9: Delete "1994" and insert --1990--.
Column 1, line 27: Delete "anthelniintic" and insert --anthelmintic--.
Column 1, line 36: Delete "toidcity" and insert --toxicity--.
Column 1, line 48: Delete "toide" and insert --toxic--.
Column 1, line 52: Delete "Ipoffo" and insert --Ignoffo--.
Column 1, line 52: Delete "Dropldn" and insert --Dropkin--.
Column 1, line 59: Delete "cytotoidc" and insert --cytotoxic--.
Column 2, line 16: Delete "genes desipated" and insert --genes designated--.
Column 2, line 37: Delete "Nonhem" and insert --Northern--.
Column 2, line 39: After "USA" insert --.--
Column 2, line 61: Delete "with aH" and insert --with all--.
Column 3, line 4: Delete "deposits wt be" and insert --deposits will be--.
Column 3, line 28: Delete "The to)dns" and insert --The toxins--.
Column 3, line 48: Delete "hke excipient" and insert --like excipient--.
Column 4, line 4: Delete "optionany" and insert --optionally--.
Column 4, line 9: Delete "Equid carrier" and insert --liquid carrier--.
Column 4, line 13: Delete "the hke" and insert --the like--.
Column 4, line 35: Delete "distier's" and insert --distiller's--.
Column 4, line 46: Delete "they wt" and insert --they will--.
Column 4, line 50: Delete "treated ceil" and insert --treated cell--.
Column 4, line 52: Delete "toidcity" and insert --toxicity--.
Column 5, line 9: Delete "Alcaligenes," and insert --Alcaligenes;--.
Column 5, line 40: Delete "to)dc" and insert --toxic--.
Column 5, line 42: Delete "to)dc" and insert --toxic--.
Column 5, line 46: Delete "wt be" and insert --will be--.

UNITED STATES PATENT AND TRADEMARK OFFICE
CERTIFICATE OF CORRECTION

PATENT NO. : 5,281,530

DATED : January 25, 1994

INVENTOR(S) : August J. Sick, George E. Schwab and Jewel Payne

It is certified that error appears in the above-indentified patent and that said Letters Patent is hereby corrected as shown below:

Column 5, line 47: Delete "Mustrative" and insert --Illustrative--.
Column 6, line 2: Delete "of Kileng" and insert --of killing--.
Column 6, line 15: Delete "cell wt" and insert --cell will--.
Column 6, line 43: Delete "The ceils" and insert --The cells--.
Column 6, line 58: Delete "au or an of the ceils" and insert --all or all of the cells--.
Column 6, line 60: Delete "Alteratively" and insert --Alternatively--.
Column 6, line 67: Delete "rice hues" and insert --rice hulls--.
Column 7, line 7: Delete "wt vary" and insert --will vary--.
Column 7, line 13: Delete "wt generally" and insert --will generally--.
Column 7, line 22: Delete "which frustrate" and insert --which illustrate--.
Column 7, line 25: Delete "afl solvent" and insert --all solvent--.
Column 7, line 66: Delete "Microbioi." and insert --Microbiol.--.
Column 7, line 67: Delete "solubilffing" and insert --solubilizing--.
Column 7, line 68: Delete "alkah" and insert --alkali--.
Column 8, line 5: Delete "Biochemistly" and insert --Biochemistry--.
Column 8, line 10: Delete "IC Gordon" and insert --K. Gordon--.
Column 8, line 14: Delete "(Hunkapffler," and insert --(Hunkapiller--.
Column 8, line 35: Delete "the ceils" and insert --the cells--.
Column 8, line 42: Delete "supermate" and insert --supernate--.

Column 8, line 54: Delete "(GCAATMAAATGAATTATATCC)." and insert --(GCAATTTTAAATGAATTATATCC)--.
Column 8, line 63: Delete "colurim" and insert --column--.
Column 8, line 67: Delete "(PROMF-GA)" and insert --(PROMEGA)--.
Column 9, line 4: Delete "vath the" and insert --with the--.
Column 9, line 19: Delete "legated" and insert --ligated--.
Column 9, line 20: Delete "The hgation" and insert --The ligation--.

UNITED STATES PATENT AND TRADEMARK OFFICE
CERTIFICATE OF CORRECTION

PATENT NO. : 5,281,530
DATED : January 25, 1994
INVENTOR(S) : August J. Sick, George E. Schwab and Jewel Payne It is certified that error appears in the above-indentified patent and that said Letters Patent is hereby corrected as shown below:

Column 9, line 22-23: Delete "ampicirin" and insert --ampicillin--.
Column 9, line 25: Delete "Mute colonies," and insert --White colonies,--.
Column 9, line 27: Delete "plasmed" and insert --plasmid--.
Column 9, line 28: Delete "plasmeds" and insert --plasmids--.
Column 9, line 28: Delete "plasmeds" and insert --plasmid--.
Column 9, line 29: Delete "EcoR1" and insert --EcoRI--.
Column 9, line 30: Delete "plasmed" and insert --plasmid--.
Column 9, line 31: Delete "EcoR1" and insert --EcoRI--.
Column 9, line 31: Delete "pNffC1628" and insert --pMYC1628--.
Column 9, line 37: Delete "The vanous" and insert --The various--.
Column 9, line 38: Delete "plasmeds" and insert --plasmids--.
Column 9, line 46: Delete "plasmed" and insert --plasmid--.
Column 9, line 47: Delete "cees, prepare plasmed" and insert --cells, prepare plasmid--.
Column 9, line 63: Delete "The legation" and insert --The ligation--.
Column 9, line 64: Delete "Plasrnids" and insert --Plasmids--.
Column 9, lines 67-68: Delete "pNffC2311 and pNffC2309" and insert --pMYC2311 and pMYC2309--.
Column 10, line 1: Delete "plasmeds" and insert --plasmids--.
Column 10, line 2: Delete "acrystaflfferous" and insert --acrystalliferous--.
Column 10, line 2: Delete "HD-1 MB" and insert --HD-1 cryB--.
Column 10, line 5: Delete "HD-1 gall" and insert --HD-1 cryB--.
Column 10, line 11: Delete "Actively" and insert --Activity--.
Column 10, line 15: Delete "coming (Coming" and insert --corning (Corning--.
Column 10, line 16: Delete "Coming, NY) 24-weH" and insert --Corning, NY) 24-well--.

UNITED STATES PATENT AND TRADEMARK OFFICE
CERTIFICATE OF CORRECTION

PATENT NO. : 5,281,530
DATED : January 25, 1994
INVENTOR(S) : August J. Sick, George E. Schwab and Jewel Payne It is certified that error appears in the above-indentified patent and that said Letters Patent is hereby corrected as shown below:

Column 10, line 19: Delete "uracfl" and insert --uracil--.
Column 11, line 9: Delete "AH DNA" and insert --All DNA--.
Column 11, line 11: Delete "MRNA" and insert --mRNA--.
Column 11, line 25: Delete "ff W is C" and insert --if W is C--.
Column 11, line 47: Delete "aB or part" and insert --all or part--.
Column 12, line 16-17: Delete "claim 17" and insert --claim 4--.

Signed and Sealed this

Sixth Day of December, 1994

Attest:

BRUCE LEHMAN

Attesting Officer     Commissioner of Patents and Trademarks